United States Patent [19]

Yoshida et al.

[11] Patent Number: 4,584,136
[45] Date of Patent: Apr. 22, 1986

[54] PROCESS FOR PREPARING ESTRACYT COMPOUNDS HAVING A CARCINOSTATIC BOUND THERETO

[75] Inventors: Masaru Yoshida; Masaharu Asano; Isao Kaetsu; Hidetoshi Yamanaka; Katsuyuki Nakai; Hisako Yuasa; Keizo Shida, all of Gunma, Japan

[73] Assignee: Japan Atomic Energy Research Institute, Tokyo, Japan

[21] Appl. No.: 707,219

[22] Filed: Mar. 1, 1985

[30] Foreign Application Priority Data

Jun. 20, 1984 [JP] Japan .................................. 59-127117

[51] Int. Cl.$^4$ ............................................... C07J 1/00
[52] U.S. Cl. ................................................... 260/397.5
[58] Field of Search ....................................... 260/397.5

[56] References Cited

U.S. PATENT DOCUMENTS 4,360,663 11/1982 Asano et al. ..................... 260/397.5

FOREIGN PATENT DOCUMENTS

WO84/02270 6/1984 PCT Int'l Appl. ............. 260/397.5

*Primary Examiner*—Elbert L. Roberts
*Attorney, Agent, or Firm*—Browdy & Neimark

[57] ABSTRACT

An Estracyt compound having a carcinostatic bound thereto is obtained by reacting an Estracyt compound with a carcinostatic having one or more radicals selected from among COOH, Cl, $NH_2$ and OH, either directly or after reaction with an amine to replace one or both Cl groups in the nitrogen mustard portion in the Estracyt compound with a $NH_2$ group, in the presence or absence of a catalyst. The resulting compound is more effective in cancer control than the Estracyt compound associated substance.

5 Claims, No Drawings

PROCESS FOR PREPARING ESTRACYT COMPOUNDS HAVING A CARCINOSTATIC BOUND THERETO

BACKGROUND OF THE INVENTION

1. Field of the Invention

The present invention relates to a process for preparing Estracyt compounds having a carcinostatic bound thereto, useful in the treatment of prostatic cancer.

2. Description of the Prior Art

Studies on hormone-dependent cancers have been considerable adavnce in recent years and one approach that is considered effective is transporting a high concentration of a hormone-based carcinostatic to a specific site in the cancer tissues and letting the carcinostatic exhibit its cancer control activity at that site. Estracyt® is the trademark for estradiol-3N-bis(2-chloroethyl)-carbamate-17β-phosphate that Ab-Leo A.G., Sweden developed in 1966 for achieving this purpose. Estracyt® has the following formula (I):

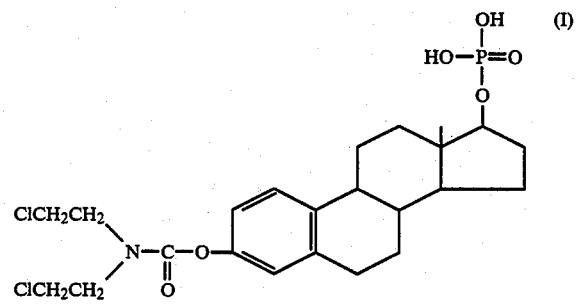

Estracyt® is a substance wherein estradiol-17β-phosphate of formula (II) has a carbamate bonding of nitrogen mustard of formula (III) at 3-position:

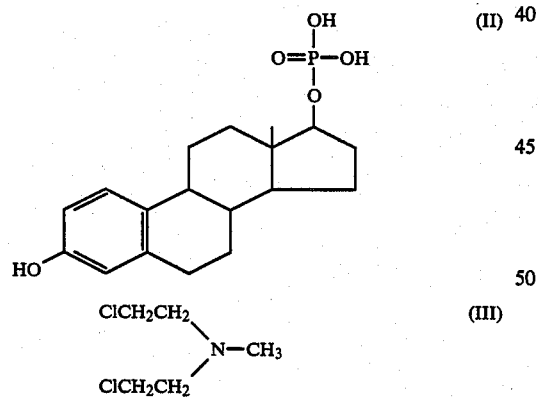

Two derivatives having the same activity as Estracyt® are estramustine of formula (IV) and estromustine of formula (V):

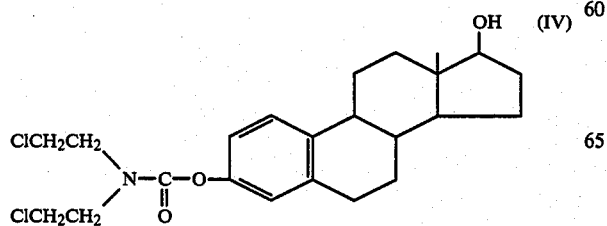

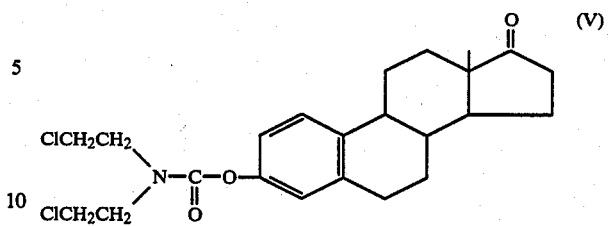

It has been reported that Estracyt®, estramustine and estromustine (hereunder collectively referred to as "Estracyt compounds"), when administered into the human body, are specifically accumulated in prostatic organs (e.g. dorsal prostate, DP; dorsolateral prostate, DLP; and seminal vesicle, SV) (see, for example, H. Yamanaka, K. Kitaura, K. Imai, H. Yuasa, K. Nakai, Y. Matsumura, H. Uehara and K. Shiba, "In Vivo Studies of $^3$H-estramustine in Castrated Male Rat", Acta Urol. Jap., 27, 243–250, 1981). It has also been reported that these Estracyt compounds are very effective in controlling progressive prostatic cancer.

Estracyt compounds may function as estrogen-cancer control agent complexes but their cancer control activities are not completely satisfactory.

SUMMARY OF THE INVENTION

The present inventors, therefore, made attempts at realizing more effective cancer treatment by combining a carcinostatic with one of the Estracyt compounds that are specifically accumulated in certain organs. As a result, the inventors have found a compound having bound thereto an agent that is more effective in cancer control than the Estracyt compound associated substance. The present invention has been accomplished on the basis of this finding.

DESCRIPTION OF THE PREFERRED EMBODIMENT

The problem stated above can be solved by a compound having an Estracyt compound bound to a carcinostatic having one or more radicals selected from among COOH, Cl, NH$_2$ and OH.

The compound in accordance with the present invention is hereunder described with particular reference to estramustine as the Estracyt compound to be bound with a carcinostatic.

In order to bind a carcinostatic to estramustine of the formula

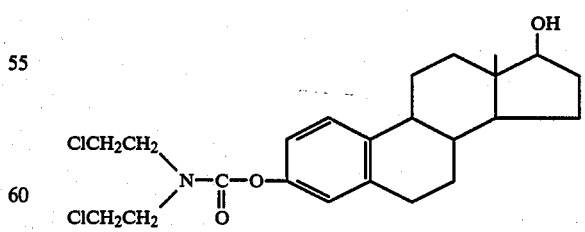

one or both Cl groups in the nitrogen mustard portion may be bound to the carcinostatic either directly or indirectly. In the indirect fashion, the nitrogen mustard may be bound to NH$_3$ or H$_2$N—(CH$_2$)$_n$—NH$_2$ so as to convert one or both Cl groups to NH$_2$ groups, as shown below.

Binding to NH₃

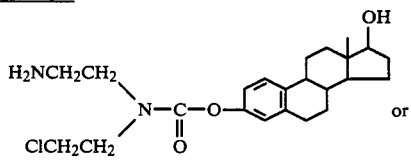 or

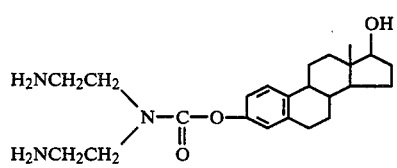

Binding to H₂N(CH₂)ₙNH₂

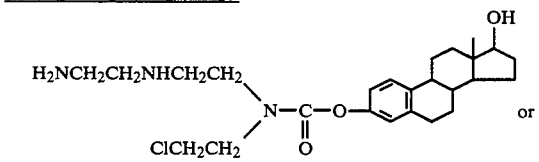 or

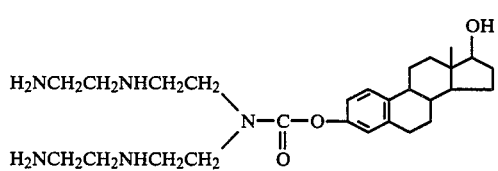

The introduction of the NH₂ group is typically done at 20°–100° C., preferably 40°–70° C. The compound having one or both Cl groups in the Estracyt compound replaced by NH₂ groups is hereunder sometimes abbreviated as Est—NH₂. The object compound of the present invention can be obtained by reacting the Est—NH₂ with a known carcinostatic having COOH, Cl, NH₂ or OH group. The specific methods for binding these radicals in carcinostatics with Est—NH₂ are carried out in the presence of a catalyst or in the absent thereof indicated below.

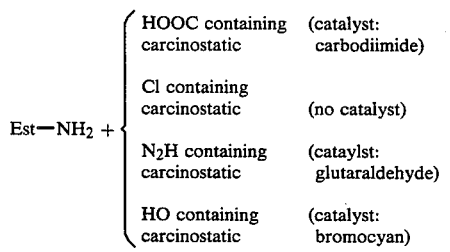

According to the present invention, the Cl group in the Estracyt compound may be directly bound to the NH₂ group in the carcinostatic, but the direct method does not achieve a very high binding efficiency. The more preferred method is the indirect one wherein the Estracyt compound is bound with a carcinostatic after one or both Cl groups in the Estracyt compound are converted to NH₂ groups.

Illustrative carcinostatics that may be bound to the Estracyt compound in accordance with the present invention are given below, with the radicals present in the carcinostatics being indicated within parentheses: chlorombucil (Cl, COOH), cyclophosphamide (Cl), mannomustine (OH, Cl), melphalan (Cl, COOH, NH₂), carbazilgunone (NH₂), cytarabine (NH₂, OH), methotrexate (NH₂, COOH), sodium aminopterin (NH₂, COOH), sarcomycin (COOH), dactinomycin (NH₂), mitomycin C (NH₂), guanylhyclrazone (NH₂) and doxorubicin hydrochloride (NH₂). Any other carcinostatics having COOH, Cl, NH₂ or OH group may be bound to the Estracyt compounds.

The advantages of the present invention are hereunder described in greater detail by reference to the following Examples.

EXAMPLE 1

Estracyt ® (0.5 g) was dissolved in a commercial aqueous NH₃ (5 ml) and phosphate buffer solution (PBS, 20 ml, pH 7.2) and the solution was heated at 50° C. for 2 days. By this treatment, the Cl portion in Estracyt ® was converted to NH₂. To the resulting Estracyt ®-NH₂, a mixture of PBS (5 ml, pH 7.2) and 0.1% glutaraldehyde solution (0.5 ml) containing 50 mg of doxorubicin hydrochloride of the formula indicated below was added:

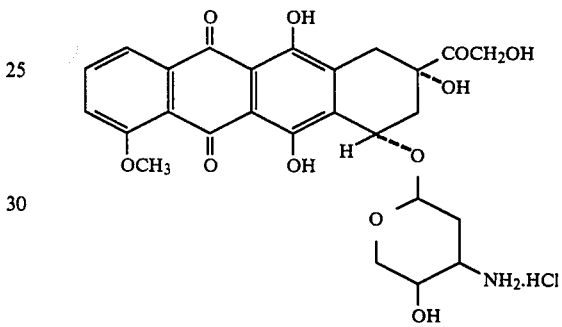

By subsequent treatment at 40° C. for 3 days, Estracyt ® was chemically bound to the NH₂ group in the doxorubicin hydrochloride.

REFERENCE EXAMPLE 1

The Estracyt ®-doxorubicin hydrochloride compound prepared in Example 1 and which contained 30 μg of Estracyt ® was injected into male Wistar rats (average weight: 400 g) through femoral blood vessels. On week later, the rats were killed and their prostatic organs (DP, DLP and SV) were removed. When 30 μg of Estracyt ® was injected alone, the contraction of the prostatic organs was negligible. On the other hand, the degree of contraction of the prostatic organs extracted from the treated group was about 40% greater than in the control group. Optical microscopic observations showed marked necrosis in the SV, DLP and VP stained with hematoxylineosin, but other organs (e.g., liver, heart, kidney, lung, spleen, pancrease and testicle) showed little sign of necrosis.

EXAMPLE 2

Estramustine (1 g) was treated with a mixture of ethylenediamine (7 ml) and ethyl alcohol (20 ml) at 50° C. for 3 days so as to convert the Cl portion in the estramustine to —NHCH₂CH₂NH₂. To the resulting estramustine—NHCH₂CH₂NH₂ compound, 10 ml of ethyl alcohol containing mitomycin C (80 mg) and 30 mg of glutaraldehyde were added, and the mixture was heated at 45° C. for 2 days. By this treatment, the estramustine was bound chemically with the NH₂ group in mitomycin C.

REFERENCE EXAMPLE 2

The estramustine-mitomicin C compound prepared in Example 2 and which contained 40 μg of estramustine was injected into male Wistar rats through femoral blood vessels. One week later, the rats were slaughtered and their prostatic organs were removed as in Reference Example 1.

Estramustine, when administered independently, caused little contraction of the prostatic organs. However, the degree of contraction of the prostatic organs extracted from the treated group was about 50% greater than in the control group. Other results were similar to those obtained in Reference Example 1.

EXAMPLE 3

Estramustine (0.5 g) was treated with a mixture of octamethylenediamine (3 g) and benzene (20 ml) at 60° C. for one day so as to convert the Cl portion in the estromustine to —$NH(CH_2)_8NH_2$. To the resulting estromustine—$NH(CH_2)_8NH_2$ 30 mg of mitomycin C and 10 ml of glutaraldehyde were added and the mixture was heated at 40° C. for 2 days. By this treatment, the estromustine was chemically bound to the $NH_2$ group in mitomycin C.

REFERENCE EXAMPLE 3

The estromustine-mitomycin C compound prepared in Example 3 and which contained 40 μg of estromustine was injected into male Wistar rats through femoral blood vessels. One week later, the rats were slaughtered and their prostatic organs were removed. The experimental results were substantially the same as in Reference Example 1.

EXAMPLE 4

An Estracyt®-chlorambucil compound was prepared as in Example 1 except that doxorubicin hydrochloride was replaced by chlorambucil and, glutaraldehyde by 1-ethyl-3-(3-dimethylaminopropyl)-carbadiimide.

REFERENCE EXAMPLE 4

The Estracyt®-chlorambucil compound prepared in Example 4 and which contained 30 μg of Estracyt® was injected into male Wistar rats through femoral blood vessels. One week later, the rats were killed and their prostatic organs were removed. The extracted organs had suffered about 20% contraction but the degree of their necrosis was substantially the same as in Reference Example 1.

What is claimed is:

1. A process for preparing an Estracyt compound having a carcinostatic bound thereto, said process comprising reacting an Estracyt compound with a carcinostatic having one or more radicals selected from among COOH, Cl, $NH_2$ and OH, either directly or after reaction with an amine to replace one or both Cl groups in the nitrogen mustard portion in the Estracyt compound with an $NH_2$ group, in the presence or absence of a catalyst.

2. A process according to claim 1 wherein the Estracyt compound is estradiol-3N-bis-(2-chloroethyl)-carbamato-17β-phosphate.

3. A process according to claim 1 wherein the Estracyt compound is estradiol-17μ-3N-bis(2-chloroethyl)-carbamate.

4. A process according to claim 1 wherein the Estracyt compound is estrone-3N-bis-(2-chloroethyl)-carbamate.

5. A process according to claim 1 wherein the catalyst is selected from the group consisting of carbodiimide, glutaraldehyde and bromocyan.

* * * * *